United States Patent
Zeng et al.

(10) Patent No.: US 8,299,125 B2
(45) Date of Patent: Oct. 30, 2012

(54) WATER-SOLUBLE TRITERPENEPHENOL COMPOUNDS HAVING ANTITUMOR ACTIVITY AND THE PREPARATION THEREOF

(75) Inventors: Jiafeng Zeng, Shanghai (CN); Junfang Pan, Shanghai (CN); Baoying Li, Shanghai (CN); Qin Zhu, Shanghai (CN); Tong Fang, Shanghai (CN); Huiyan Ni, Shanghai (CN)

(73) Assignee: Shanghai Huatuo Medical Science Co., Ltd., Shanghai (CN)

( * ) Notice: Subject to any disclaimer, the term of this patent is extended or adjusted under 35 U.S.C. 154(b) by 368 days.

(21) Appl. No.: 12/743,101

(22) PCT Filed: Nov. 5, 2008

(86) PCT No.: PCT/CN2008/072959
§ 371 (c)(1),
(2), (4) Date: May 14, 2010

(87) PCT Pub. No.: WO2009/067891
PCT Pub. Date: Jun. 4, 2009

(65) Prior Publication Data
US 2010/0267983 A1    Oct. 21, 2010

(30) Foreign Application Priority Data
Nov. 16, 2007    (CN) .......................... 2007 1 0170537

(51) Int. Cl.
*C07C 309/27*    (2006.01)
*A61K 31/216*    (2006.01)
*A61K 31/192*    (2006.01)
(52) U.S. Cl. ........... 514/569; 514/532; 560/11; 562/498
(58) Field of Classification Search .................. 514/532, 514/569; 560/11; 562/498
See application file for complete search history.

(56) References Cited

FOREIGN PATENT DOCUMENTS
WO    2007077203 A2    7/2007
WO    2007117466 A2    10/2007

OTHER PUBLICATIONS

Brown et al. J.C.S. Perkin I, 1973, 2721-2725.*
Fang-Rong Chang et al., "Antitumor Agents. 228. Five New Agarofurans, Reissantins A-E, and Cytotoxic Principles from *Reissantia buchananii*," J. Nat. Prod., 2003, 66, pp. 1416-1420.
Todd R. Furbacher et al., "Catalytic Inhibition of Topoisomerase IIa by Demethylzeylasterone, a 6-Oxophenolic Triterpenoid from *Kokoona zeylanica*," J. Nat. Prod., 2001, 64, pp. 1294-1296.
Felix M. Rodriguez, "New phenolic triterpenes from *Maytenus blepharodes*. Semisynthesis of 6-deoxoblepharodol from pristimerin," Science Direct, Tetrahedron 61 (2005) pp. 2513-2519.
Anita Ankli et al., "Cytotoxic cardenolides and antibacterial terpenoids from *Crossopetalum gaumeri*," Phytochemistry 54 (2000), pp. 531-537.
Yoshihisa Takaishi et al., "Triterpenoid Inhibitors of Interleukin-1 Secretion and Tumour-Promotion from *Tripterygium wilfordii* Var, *Regelii*," Phytochemistry, vol. 45, No. 5, pp. 969-974 (1997).
Masahiro Nagase et al., "Apoptosis Induction in HL-60 Cells and Inhibition of Topoisomerase II by Triterpene Celastrol," Biosci. Biotechnol. Biochem., 67 (9), pp. 1883-1887 (2003).
Chinese Office Action for 200710170537.2 dated Sep. 13, 2010.
EP Search Report for 08855158.5 dated Nov. 11, 2010.
EP Communication (Form 2004) for 08855158.5 dated Dec. 16, 2011.
ISR for PCT/CN2008/072959 dated Feb. 19, 2009.

* cited by examiner

*Primary Examiner* — Joseph Kosack
*Assistant Examiner* — Matthew Coughlin
(74) *Attorney, Agent, or Firm* — Lowe, Hauptman, Ham & Berner, LLP

(57) ABSTRACT

The invention discloses water-soluble triterpenephenol compounds having antitumor activity represented by formula (I), wherein the substituents $R_1 \sim R_4$ and M are defined as in the description. The invention also discloses a method for preparing the compounds of formula (I) used quinone methide triterpene compounds as starting materials. The water-soluble triterpenephenol compounds disclosed in the invention can be made into various dosage forms including injection, tablet, capsule, granule and liniment, particularly suitable for making into injection.

9 Claims, No Drawings

WATER-SOLUBLE TRITERPENEPHENOL COMPOUNDS HAVING ANTITUMOR ACTIVITY AND THE PREPARATION THEREOF

RELATED APPLICATIONS

The present application is national phase of International Application No. PCT/CN2008/072959, filed Nov. 5, 2008, and claims priority from, Chinese Application Number CN200710170537.2, filed Nov. 16, 2007, the disclosures of which are hereby incorporated by reference herein in their entirety.

FIELD OF THE INVENTION

The invention relates to triterpenephenol compounds, more particularly, relates to water-soluble triterpenephenol compounds having antitumor activity and the preparation thereof.

BACKGROUND OF THE INVENTION

Cancer is a serious disease against human health and has become the first disease causing people to die. Currently, people dying of cancer are about 1,400,000~1,500,000 in China every year, and it is estimated that cancer causes an economic loss of 14 billions every year. Treatment with antitumor drugs is one of the major methods for tumor therapy. Natural products are important resources for the discovery of new antitumor drugs, and lead compounds of many antitumor drugs are obtained from nature, such as vinblastine, vincristine, camptothecin and paclitaxel, etc. However, these compounds need to be structurally modified and improved to be used as clinical antitumor drugs due to their problems in toxic side effects, solubility and stability, etc.

Quinone methide triterpene compounds are a class of natural compounds having antitumor activity. The unique quinone methide structure in the A ring thereof endows these compounds with antitumor activity, but also with easy polymerization, high sensitivity to pH in a solution, and instability under basic or acid conditions so as to easily take place various reactions such as ring-opening, rearrangement, etc. [reference 1: K. Nakanishi, Y. Takahashi and H. Budzikiewicz, Pristimerin. Spectroscopic Properties of the Dienone-Phenol-Type Rearrangement Products and other Derivatives. J. Org. Chem. 30:1729 (1965)]. Natural quinone methide triterpene compounds are fat-soluble, and hardly soluble in water, and thus difficult to be administered intravenously.

SUMMARY OF THE INVENTION

To address the above-said technical problems, the invention provides a class of water-soluble triterpenephenol compounds with sulfonic group at 6-position which forms salts, so as to overcome the defect that the quinone methide triterpene compounds are highly sensitive to pH, and improve the water solubility greatly.

Another object of the invention is to provide a method for preparing the above water-soluble triterpenephenol compounds.

The invention provides a class of water-soluble triterpenephenol compounds having antitumor activity represented by the following formula:

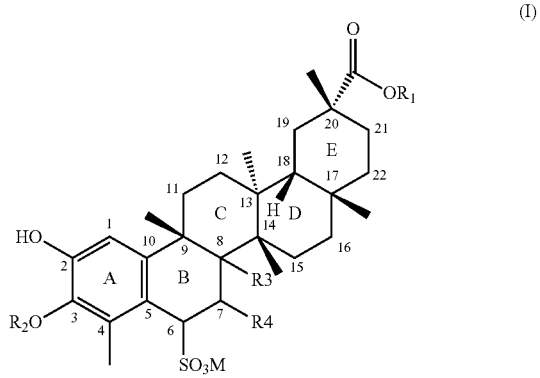

wherein, $M=Na, K, NH_4$ or $Ca$;
$R_1=H$ or $C_1$-$C_{12}$ alkyl;
$R_2=H$, $C_1$-$C_{12}$ alkyl or $C_1$-$C_{12}$ acyl, and the like;
$R_3$ and $R_4$ are H or OH, or $R_3$ is H, and $R_4$ is O=, or
the carbon atoms at 7- and 8-position where $R_3$ and $R_4$ locate respectively form a double bond.

The invention also relates to the crystalline hydrate of the compounds (I) and the pharmaceutical dosage forms of the compounds (I).

The invention further provides a method for preparing the compounds (I) comprising the steps of:

a) dissolving quinone methide triterpene compounds in water-miscible organic solvents; mixing well with solution of bisulfites; stirring the mixture at room temperature until the reaction solution is approximately colorless; concentrating to dryness under reduced pressure at a temperature less than 40° C. to obtain a raw product, as illustrated in the following scheme:

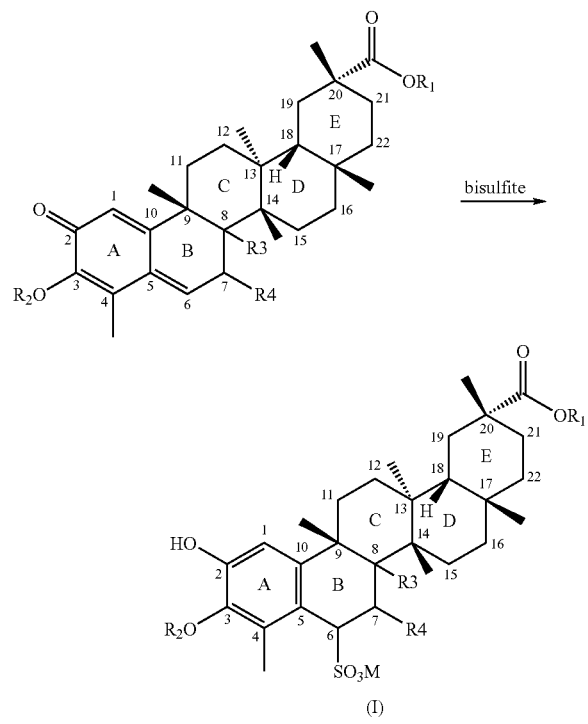

b) dissolving the raw product obtained in step a) by addition of methanol, absolute ethanol or isopropanol, and filtering; concentrating the filtrate to dryness under reduced pressure at a temperature less than 40° C.; re-crystallizing the obtained solid from solvents at a temperature in the range of 0 to 4° C. to afford a white crystal; and filtering to obtain the final product.

DETAILED DESCRIPTION

In the above preparation method, the quinone methide triterpene compounds refers to the triterpene compounds with a carbonyl group at 2-position, double bonds between the carbon atoms of 1- and 10-position, 3- and 4-position and 5- and 6-position, a methyl at 4-position, and a hydroxyl or an alkoxy or an acyloxy at 3-position.

In the above step a), the water-miscible organic solvents for dissolving the quinone methide triterpene compounds is selected from the group consisting of acetone, methanol, ethanol, isopropanol and tetrahydrofuran, preferably ethanol. The bisulfites is selected from the group consisting of sodium bisulfite, potassium bisulfite, ammonium bisulfite and calcium bisulfite, preferably sodium bisulfite.

In the above preparation method, the molar ratio of the quinone methide triterpene compound to the bisulfite is 1:1~1.2, preferably 1:1.1.

In the above step b), the solvents for recrystallization is selected from the group consisting of methanol, ethanol, chloroform-methanol, acetone-water, methanol-water, ethanol-water, isopropanol-water and tetrahydrofuran-water, preferably ethanol-water.

The compound (I) of the invention may be made into various pharmaceutical dosage forms, including injection, tablet, capsule, granule and liniment, particularly suitable for making into injection.

The in vivo pharmacologic tests of the invention showed that the compounds have significant inhibition activiy against the growth of human prostate cancer cells PC-3 transplanted into nude mice. The human prostate cancer cells PC-3 is the cells line for screening antitumor drugs. The compounds have therapeutic effects against various solid tumors, adenomas and hematological malignancies, and are especially suitable for treating hematological malignancies, such as chronic myelogenous leukaemia, multiple myeloma, since they can be administered intravenously.

ADVANTAGEOUS EFFECT OF THE INVENTION

The compounds have excellent water solubility to be formulated into a stable solution so that they are especially suitable to be administered intravenously, and possess good antitumor activity.

EXAMPLES

The invention will be further described below with reference to specific examples. However, these examples should not be construed to limiting the scope of the present invention.

Example 1

Preparation of Compound a from Celastrol as a Raw Material 20.5 mg of celastrol was dissolved in 1 ml of acetone, and then 0.5 ml of aqueous solution of sodium bisulfite (containing 5.66 mg of sodium bisulfite) was added thereinto. The reaction mixture was stirred until it became colorless and transparent. Then it was concentrated to dryness under reduced pressure at 40° C. to give a white powder. After isopropanol was added to dissolve the white powder, the solution was filtered, and the filtrate was concentrated to dryness under reduced pressure at a temperature less than 40° C. The residue was recrystallized from ethanol-water at a temperature in the range of 0 to 4° C. to afford a white crystal. After filtration under reduced pressure, 20.8 mg of white acicular crystal was obtained.

Example 2

Preparation of Compound a from Celastrol as a Raw Material 502 mg of celastrol was dissolved in 10 ml of ethanol, and then 5 ml of aqueous solution of sodium bisulfite (containing 128 mg of sodium bisulfite) was added thereinto. After stirring for 1 hour, the solution became approximately colorless and transparent, and then was concentrated to dryness under reduced pressure at 40° C. to obtain a white powder. After absolute ethanol was added to dissolve the white powder, the solution was filtered, and the filtrate was concentrated to dryness under reduced pressure at a temperature less than 40° C. The residue was recrystallized from ethanol-water at a temperature in the range of 0 to 4° C. to afford a white crystal. After filtration under reduced pressure, 516 mg of white acicular crystal was obtained.

Analytic Results:

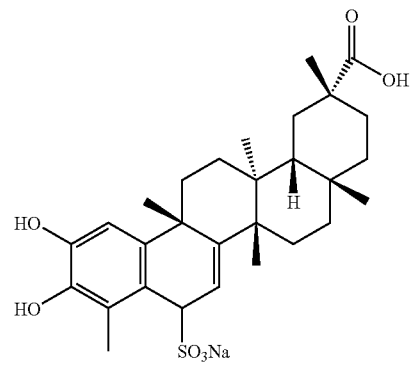

A

The NMR Spectrum of Compound A:

$^1$H NMR (DMSO-$d_6$, 300M), δ 12.01 (1H, s, —COOH), 8.81 (1H, s, —OH), 7.62 (1H, s, —OH), 6.58 (3H, s, H-1), 5.81 (1H, d, J=6.2 Hz, H-7), 4.49 (1H, d, J=6.2 Hz, H-6), 2.21 (3H, s. 23-CH$_3$), 1.62 (3H, s, 25-CH$_3$), 1.18 (3H, s, 26-CH$_3$), 1.09 (3H, s, 30-CH$_3$), 1.05 (3H, s, 28-CH$_3$), 0.59 (3H, s, 27-CH$_3$).

$^{13}$C NMR (DMSO, 300M), δ 179.87 (C-29), 149.03 (C-8), 143.68 (C-2), 141.57 (C-10), 140.54 (C-3), 122.85 (C-4), 121.44 (C-5), 118.30 (C-7), 108.67 (C-1), 59.79 (C-6), 44.03 (C-18), 43.56 (C-14), 39.50 (C-20), 37.67 (C-9), 37.50 (C-13), 36.60* (C-11), 36.60* (C-16), 34.76* (C-22), 34.41 (C-25), 32.63 (C-30), 31.55 (C-28), 30.21 (C-12), 30.21 (C-17), 30.21 (C-19), 29.7 (C-21), 28.65 (C-15), 21.21 (C-26), 18.04 (C-27), 13.19 (C-23). * represents that the assignment may be possibly exchangeable.

The MS of compound A: ESI-MS (negative ion mode): m/z 531.7.

Example 3

Preparation of Compound a from Celastrol as a Raw Material 10.58 g of celastrol was dissolved in 100 ml of ethanol, and then 50 ml of aqueous solution of sodium bisulfite (containing 2.64 g of sodium bisulfite) was added thereinto. After stirring for 1 hour, the solution became approximately colorless and transparent, and was then concentrated to dryness under reduced pressure at 40° C. to give a white powder. After absolute ethanol was added to dissolve the white powder, the solution was filtered, and the filtrate was concentrated to dryness under reduced pressure at a temperature less than 40° C. 170 ml of absolute ethanol and 7 ml of water were added to dissolve the residue ultrasonically, and the solution was left standing at a temperature in the range of 0 to 4° C. to isolate a white crystal. After filtration, 11.4 g of final product was obtained.

Example 4

Preparation of Compound B from Pristimerin as a Raw Material 19.5 mg of pristimerin was dissolved in 1 ml of ethanol, and then 0.5 ml aqueous solution of sodium bisulfite (containing 4.80 mg of sodium bisulfite) was added thereinto. After stirring for 1 hour, the solution became colorless and transparent, and was then concentrated to dryness under reduced pressure at 40° C. to give a white powder. After isopropanol was added to dissolve the white powder, the solution was filtered, and the filtrate was concentrated to dryness under reduced pressure at a temperature less than 40° C. The residue was recrystallized from ethanol-water. After filtration, 19.2 mg of white acicular crystal was obtained.

Analytic results:

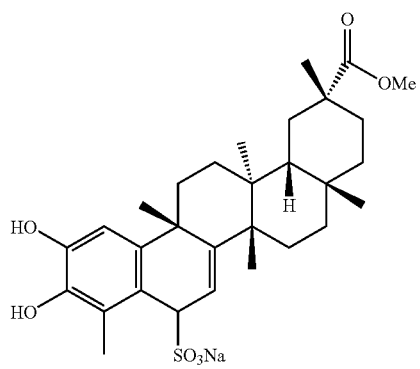

The $^1$H NMR Spectrum of Compound B:

$^1$H NMR (DMSO-$d_6$, 300M), δ 8.72 (1H, br s, —OH), 7.58 (1H, br s, —OH), 6.53 (3H, s, H-1), 5.79 (1H, d, J=5.6 Hz, H-7), 4.43 (1H, d, J=5.6 Hz, H-6), 2.20 (3H, s. 23-CH$_3$), 1.62 (3H, s, 25-CH$_3$), 1.18 (3H, s, 26-CH$_3$), 1.10 (3H, s, 30-CH$_3$), 1.06 (3H, s, 28-CH$_3$), 0.42 (3H, s, 27-CH$_3$).

Example 5

The Following Compounds were Prepared Using the Same Method

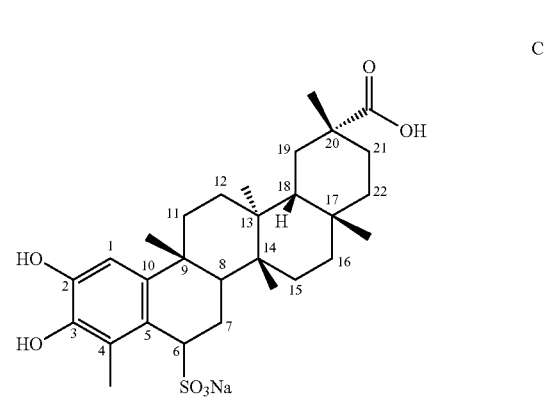

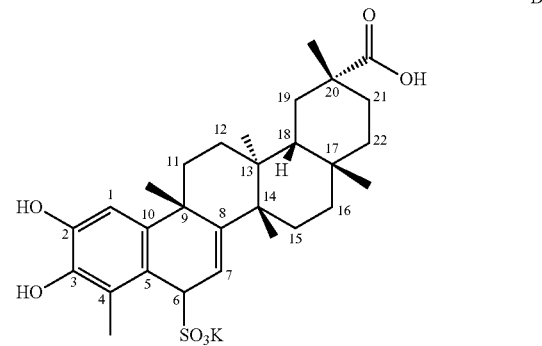

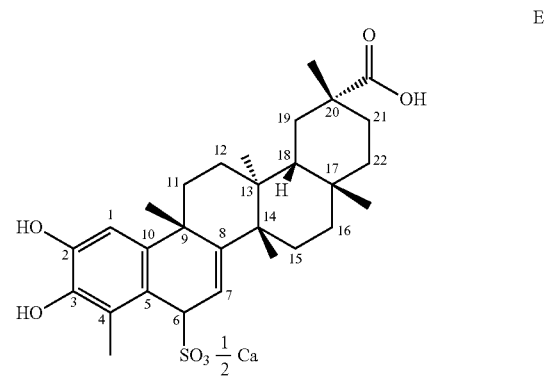

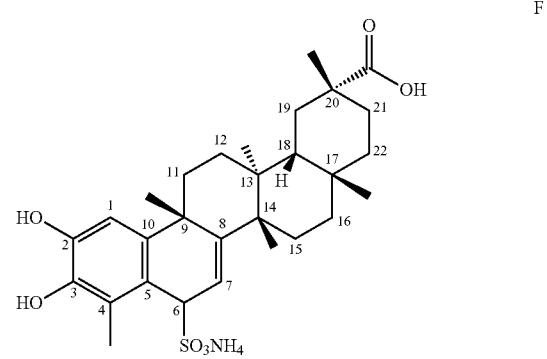

-continued

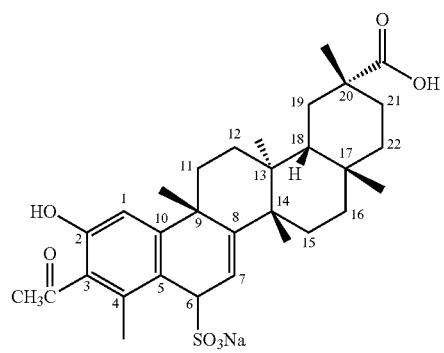

G

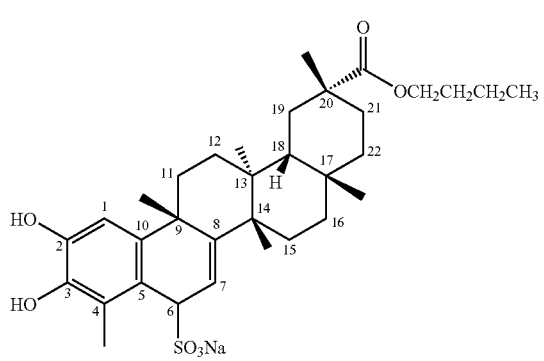

H

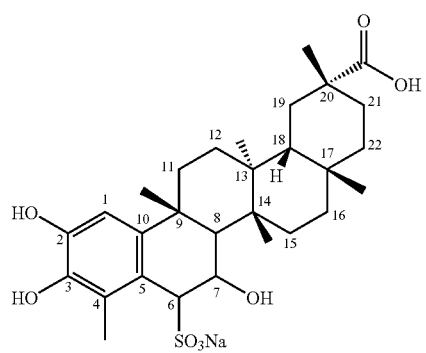

I

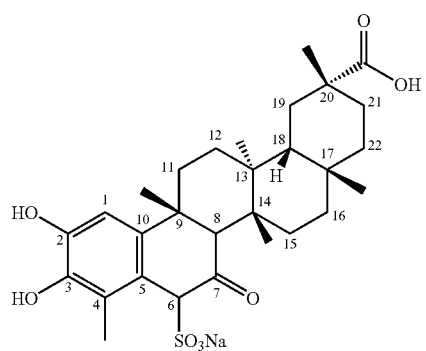

J

Example 6

Preparation of an Injection of Compound A 3.7 g of compound A and 5 g of sodium bisulfite were dissolved in 10 L of water, and the solution was filtered through a micro-pore filter film having a pore diameter of 0.22 μm. The filtered solution was distributed into vials having a volume of 7 ml with 3 ml/vial. The vials were then sealed with rubber plugs and aluminium caps, and treated with moist heat sterilization at 116° C. for 30 min to provide the final product.

Example 7

Stability Assay of Compound A During the Preparation of the Injection

Experimental conditions: the chromatography column was DIKMA C18 column (5μ, 250×4.6 mm); the detector was Agilent 1100 DAD detector; the detection wavelength was 210 nm; the liquid phase was acetonitrile-0.02M $KH_2PO_4$ (which contains 1‰ of tetrabutylammonium hydroxide, and the pH was adjusted to 7.35 with triethylamine) (35:65); the flow speed was 1 ml/min; and sample amount was 20 μl.

Sample: the solutions in each step of the preparation of the injection of compound A in example 6

Experimental data: the peak area of the solution before filtering with micro-pore filter film was 1084.4, the peak area after filtering was 1078.2, and the peak area after the moist heat sterilization was 1072.9.

The experimental results showed that the stability of compound A is good during the injection preparation.

Example 8

Stability Assay of the Injection of Compound A

Experimental conditions: the chromatography column was DIKMA C18 column (5μ, 250×4.6 mm); the detector was Waters 3487 detector; the detection wavelength was 210 nm; the liquid phase was acetonitrile-0.02M $KH_2PO_4$ (which contains 1‰ of tetrabutylammonium hydroxide, and the pH was adjusted to 7.35 with triethylamine) (35:65); and the flow speed was 1 ml/min.

Experimental method: the injection prepared in example 6 was reserved at a temperature in the range of 0 to 5° C. 1 ml of the injection was taken precisely at 0 day, 7 days, 14 days, 21 days, 30 days and 45 days respectively, and diluted to 5 ml with water to afford the sample solution. 20 μl of each sample solution and control solution were injected into the chromatograph respectively, and the peak areas were recorded to calculate the content of sample solutions.

Experimental data are shown in the following table 1.

TABLE 1 detection of the stability of the injection of compound A

| Observation time | Assay items | | |
|---|---|---|---|
| | Appearance | pH | content of A (mg/ml) |
| 0 day | colorless and transparent liquid | 4.16 | 0.3707 |
| 7 days | colorless and transparent liquid | 4.18 | 0.3664 |
| 14 days | colorless and transparent liquid | 4.15 | 0.3695 |
| 21 days | colorless and transparent liquid | 4.12 | 0.3715 |
| 30 days | colorless and transparent liquid | 4.15 | 0.3687 |
| 45 days | colorless and transparent liquid | 4.13 | 0.3673 |

The experimental results showed that the injection solution has good stability.

Example 9

Stability Assay of Compound A at Meta-Acidic Condition or Meta-Alkalescence Condition Experimental conditions: the chromatography column was DIKMA C18 column (5μ, 250×4.6 mm); The detector was Waters 3487 detector; the detection wavelength was 210 nm; the liquid phase was acetonitrile-0.02M $KH_2PO_4$ (which contains 1‰ tetrabutylammonium hydroxide, and the pH was adjusted to 7.35 with triethylamine) (35:65); and the flow speed was 1 ml/min.

Experimental method: the compound A was formulated into a solution of about 5 mg/ml with distilled water. 0.1 ml of the solution was added into the following solutions respectively: a) 1 ml of HCl diluted solution with a pH of 2; b) 1 ml of distilled water; c) 1 ml of sodium carbonate diluted solution with a pH of 10. After left standing at room temperature for 2 hours, 0.1 ml of each the above three kinds of solution were added into 1 ml of liquid phase solution, respectively, and 20 μl was sampled and injected into the chromatograph. The peak areas were then determined and calculated.

The experimental results are shown in the following table 2.

TABLE 2

| the comparison of the stability of compound A at pH meta-acidic condition and meta-alkalescence condition respectively | | | |
|---|---|---|---|
| Compound A | pH = 2 | Distilled water | pH = 10 |
| Peak area | 1247385 | 1206926 | 1232216 |
| Percentage* | 103.4% | 100% | 102.1% |

*it was calculated based on the peak area in distilled water which is taken as 100%.

The experimental results showed that the compound A has good stability at both meta-acidic condition and meta-alkalescence condition.

Example 10

The Pharmacologic Activity Experiment of Compound A In Vivo

The therapeutic activity experiment of compound A against human prostate cancer cell PC-3 transplanted into nude mice was conducted by SHANGHAI INSTITUTE OF MATERIA MEDICA, CHINESE ACADEMY OF SCIENCES, under assignment by SHANGHAI HUATUO MEDICAL SCIENCE CO., LTD.

Tested Compound: Compound A.

Positive control medicine: mitomycin (MMC), produced by Kyowa Hakko kogyo Co Ltd. (batch no: 468AEF, 2 mg/bottle), was diluted with physiological saline when used.

Animal and transplanted tumor: BALB/Ca nude mice, female, 45~50 days old, weight 20±1 g. The transplanted tumor of human prostate cancer cell PC-3 in nude mice was established by inoculating the nude mice with PC-3 cell line subcutaneously.

Evaluation Method:

TV ($mm^3$) is the tumor volume, and the calculation equation is: $TV = \frac{1}{2} \times a \times b^2$, wherein a and b represent length and width respectively. $d_0$ is the tumor volume measured as medicine is administered in divided cages, and $d_{24}$ is the tumor volume on the $24^{th}$ day of the experiment. RTV is the relative tumor volume, and the calculation equation is $RTV = V_t/V_0$, wherein $V_0$ is the tumor volume measured as medicine is administered in divided cages (i.e. $d_0$), $V_t$ is the tumor volume measured every time. The evaluation index of the antitumor activity is the relative tumor proliferation rate T/C (%) and the calculation equation is as follows:

$$T/C(\%) = (TRTV/CRTV) \times 100$$

TRTV: RTV of the therapeutic group; CRTV: RTV of the negative control group.

Evaluation standard of therapeutic effect: T/C (%)>60% is ineffective, T/C (%)≦60 and with a statistic result of p<0.05 represents effective.

The results of the pharmacologic experiments are shown in the following table 3.

TABLE 3

| | | | | | | | | |
|---|---|---|---|---|---|---|---|---|
| the therapy effects of compound A against human prostate cancer cells PC-3 transplanted into nude mice | | | | | | | | |
| Group | dosage | Administering form | Number of animal | TV ($mm^3$) $d_0$ | TV ($mm^3$) $d_{24}$ | RTV | T/C (%) | P value |
| Negative control (physiological saline) | 0.2 ml/mouse | i.p | 12 | 141 ± 51 | 1178 ± 218 | 9.3 ± 3.5 | | |
| Positive control (mitomycin) | 5 mg/kg, dl/3.5 w | i.p | 6 | 135 ± 42 | 400 ± 224 | 3.1 ± 1.8 | 33.7 | <0.05 |
| A | 3 mg/kg, dl/3.5 w | i.p | 6 | 135 ± 16 | 501 ± 133 | 3.8 ± 1.1 | 40.2 | <0.05 |

The experimental results showed that compound A has marked inhibition effects on the growth of human prostate cancer cell PC-3 transplanted into nude mice.

The invention claimed is:

1. A water-soluble triterpenephenol compound represented by the following formula:

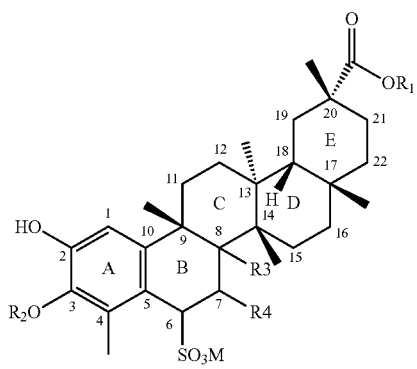

(I)

wherein,
$R_2$=H, $C_1$-$C_{12}$ alkyl or $C_1$-$C_{12}$ acyl;
M=Na, K, $NH_4$ or ½Ca;
$R_1$=H or $C_1$-$C_{12}$ alkyl;
$R_3$ and $R_4$ are H or OH, or $R_3$ is H, and $R_4$ is (O=), or the carbon atoms at the 7- and 8-positions where $R_4$ and $R_3$ are respectively located form a double bond.

2. A method for preparing a compound of claim 1, comprising the following steps of:

a) dissolving a quinone methide triterpene compound in a water-miscible organic solvent; mixing well with a solution of bisulfite; stirring the mixture at room temperature until the reaction solution becomes approximately colorless; concentrating to dryness under reduced pressure at a temperature less than 40° C. to obtain a raw product, as illustrated in the following scheme:

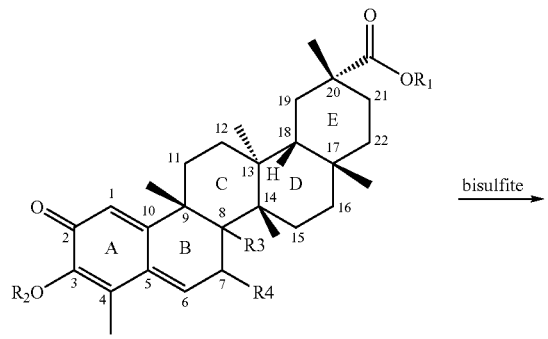

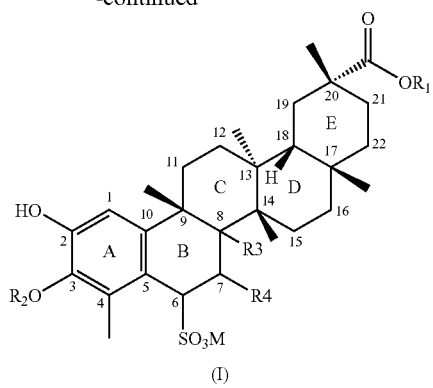

(I)

b) dissolving the raw product obtained in step a) by addition of an organic solvent and filtering; concentrating the filtrate to dryness under reduced pressure at a temperature less than 40° C.; recrystallizing the obtained solid from solvent at a temperature in the range of 0 to 4° C. to afford a white crystal; and filtering to obtain the final product of formula (I).

3. The preparation method of claim 2, wherein, said water-miscible organic solvent in step a) is selected from the group consisting of acetone, methanol, ethanol, isopropanol and tetrahydrofuran.

4. The preparation method of claim 2, wherein, said bisulfite is selected from the group consisting of sodium bisulfite, potassium bisulfite, ammonium bisulfite and calcium bisulfite.

5. The preparation method of claim 2, wherein, the molar ratio of the quinone methide triterpene compound to the bisulfite in step a) is 1:1 to 1.2.

6. The preparation method of claim 2, wherein, the organic solvent added after concentrating the filtrate to dryness under reduced pressure at a temperature less than 40° C. in step a) is selected from the group consisting of methanol, absolute ethanol and isopropanol.

7. The preparation method of claim 2, wherein, the solvent for recrystallization is selected from the group consisting of methanol, ethanol, chloroform-methanol, acetone-water, methanol-water, ethanol-water, isopropanol-water and tetrahydrofuran-water.

8. The compound of claim 1, wherein, said compound is prepared into the form of an injection, tablet, capsule, granule or liniment.

9. A method of treating prostate cancer comprising administering to a human subject in need thereof an effective amount of a compound of claim 1.

* * * * *